United States Patent
Kato et al.

(10) Patent No.: US 7,199,993 B2
(45) Date of Patent: Apr. 3, 2007

(54) ION-GENERATING COMPONENT, ION-GENERATING UNIT, AND ION-GENERATING APPARATUS

(75) Inventors: Shinji Kato, Osaka-fu (JP); Yoshihiro Sako, Shiga-ken (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 144 days.

(21) Appl. No.: 10/851,568

(22) Filed: May 24, 2004

(65) Prior Publication Data
US 2005/0036266 A1    Feb. 17, 2005

(30) Foreign Application Priority Data
Aug. 13, 2003   (JP) .............................. 2003-292873

(51) Int. Cl.
*H01T 23/00* (2006.01)
*H05F 3/06* (2006.01)
(52) U.S. Cl. .................. 361/231; 361/230; 361/229
(58) Field of Classification Search ................ 361/231, 361/230, 229
See application file for complete search history.

(56) References Cited

U.S. PATENT DOCUMENTS

| | | | |
|---|---|---|---|
| 3,418,501 A * | 12/1968 | Felici et al. ................ 310/309 |
| 4,417,293 A | 11/1983 | Larigaldie | |
| 4,673,416 A * | 6/1987 | Sakakibara et al. ............. 96/79 |
| 4,686,370 A * | 8/1987 | Blach ...................... 250/423 R |
| 5,079,669 A * | 1/1992 | Williams ..................... 361/235 |
| 5,114,677 A * | 5/1992 | Steele et al. .................. 422/83 |
| 5,377,070 A * | 12/1994 | Kawamoto ................... 361/229 |
| 6,040,055 A * | 3/2000 | Baba et al. .................. 428/428 |
| 2002/0048818 A1* | 4/2002 | Sakairi et al. ............. 436/126 |

FOREIGN PATENT DOCUMENTS

| | | |
|---|---|---|
| EP | 0 373 869 | 6/1990 |
| EP | 0 525 193 | 2/1993 |
| JP | 06-181087 | 6/1994 |

OTHER PUBLICATIONS

Official Communication dated Dec. 7, 2005, issued in the corresponding European Patent Application No. 04 012 775.5-2301.

* cited by examiner

*Primary Examiner*—Brian Sircus
*Assistant Examiner*—Z Kitov
(74) *Attorney, Agent, or Firm*—Keating & Bennett, LLP

(57) ABSTRACT

An ion-generating component has, on an insulating substrate, a ground electrode, a high-voltage electrode, an insulating film provided on the surface of the ground electrode, and a wire electrode. A cutout is formed by cutting out one side of the insulating substrate. The root of the wire electrode is soldered to the high-voltage electrode, and the leading end thereof is positioned near the cutout. The wire electrode is made of an ultrafine wire having a diameter of about 100 μm or less, for example, a piano wire, a tungsten wire, a stainless wire, or a titanium wire.

13 Claims, 8 Drawing Sheets

ION-GENERATING COMPONENT, ION-GENERATING UNIT, AND ION-GENERATING APPARATUS

BACKGROUND OF THE INVENTION

1. Field of the Invention

The present invention relates to an ion-generating component, and more particularly, to an ion-generating component used in a negative-ion generating circuit of an air cleaner or an air conditioner, and an ion-generating unit and an ion-generating apparatus including the ion-generating component.

2. Description of the Related Art

This type of ion-generating apparatus is disclosed in Japanese Unexamined Patent Application Publication No. 6-181087. FIG. 8 shows the ion-generating apparatus. As shown in FIG. 8, an ion-generating apparatus 110 includes a housing 120, a discharging electrode 112 mounted on the front surface of the housing 120, and a counter electrode 114. A high-voltage power supply 118 is disposed at the top of the housing 120. The high-voltage power supply 118 includes a high-voltage generating circuit that applies a high alternating voltage between the discharging electrode 112 and the counter electrode 114.

The discharging electrode 112 has a plurality of sawteeth 112a, and is disposed perpendicularly to the counter electrode 114. The counter electrode 114 is fixed to a bottom portion 120b of the housing 120, and has a structure in which metal is embedded in a dielectric ceramic material. The discharging electrode 112 and the counter electrode 114 act to generate ozone by discharging and to convert air into negative ions by the application of a high alternating voltage.

However, in the known ion-generating apparatus 110, a high voltage of −5 kV to −7 kV must be applied to the discharging electrode 112 in order to generate negative ions. For this reason, the power supply circuit and the insulating structure are complicated, and the production cost of the ion-generating apparatus 110 is increased.

Furthermore, when a high voltage of −5 kV to −7 kV is applied to the discharging electrode 112, ozone is incidentally generated, and therefore, it is impossible to selectively generate only negative ions. Moreover, since a high voltage is applied to the discharging electrode 112, there is a need to take sufficient safety measures.

In addition, since the discharging electrode 112 and the counter electrode 114 perpendicularly oppose each other (arranged three-dimensionally), the occupied volume is large, and size reduction of the ion-generating apparatus 110 is difficult.

SUMMARY OF THE INVENTION

In order to overcome the problems described above, preferred embodiments of the present invention provide an ion-generating component, an ion-generating unit, and an ion-generating apparatus that can generate negative ions by the application of a low voltage.

According to a preferred embodiment of the present invention, an ion-generating component includes an insulating substrate, a wire electrode having a diameter of about 100 μm or less and mounted on the insulating substrate, and a ground electrode opposing the wire electrode.

Since the wire electrode has a small diameter of about 100 μm or less, electrons easily concentrate at the leading end thereof, and an intense electric field is easily produced.

Preferably, the ground electrode is provided on the insulating substrate. Furthermore, preferably, the ground electrode is disposed substantially parallel to the longitudinal direction of the wire electrode. More specifically, the insulating substrate preferably has a cutout at one side, the leading end of the wire electrode is positioned near the cutout, and the ground electrode has two legs extending substantially parallel to the wire electrode and on both sides of the cutout and the wire electrode.

The above-described structures allow the wire electrode and the ground electrode to be arranged two-dimensionally, and the thickness of the ion-generating component can be reduced.

Preferably, the ground electrode is disposed substantially perpendicularly to the longitudinal direction of the wire electrode. The above-described structure increases the flexibility in arranging the wire electrode and the ground electrode.

Preferably, a surface of the ground electrode is covered with an insulating film. This can reduce the generation of ozone without substantially changing the number of generated negative ions. Preferably, the ground electrode is made of a resistor such as a ruthenium oxide or carbon resistor. This is because the resistor can reduce the dangers of heat generation and firing due to short-circuiting, for example, even when the wire electrode touches the ground electrode. Especially, ruthenium oxide is the optimum material because it does not cause migration even when an intense electric field is applied thereto.

According to another preferred embodiment of the present invention, an ion-generating unit includes an ion-generating component having the above-described features, a high-voltage electrode provided on the insulating substrate and connected to the wire electrode, a first terminal connected with the high-voltage electrode and having a retaining portion for a lead wire, a second terminal connected with the ground electrode and having a retaining portion for another lead wire, and a case for accommodating the ion-generating component, the high-voltage electrode, the first terminal, and the second terminal.

According to a further preferred embodiment of the present invention, an ion-generating apparatus includes the above-described ion-generating component, and a high-voltage power supply for generating a negative voltage.

Alternatively, another preferred embodiment of the present invention provides an ion-generating apparatus including an ion-generating unit having lead wires retained by the first terminal and the second terminal, and having the above-described features, and a high-voltage power supply for generating a negative voltage. It is preferable that the absolute value of the voltage output from the high-voltage power supply be about 2.5 kV or less.

The above-described features make it possible to obtain a small and low-cost ion-generating unit or ion-generating apparatus.

Since the ion-generating component of various preferred embodiments of the present invention uses a thin wire electrode having a diameter of about 100 μm or less, electrons easily concentrate at the leading end of the wire electrode, and an intense electric field is easily produced. Therefore, negative ions can be generated by the application of a voltage lower than before. As a result, it is possible to obtain a small and low-cost ion-generating unit or ion-generating apparatus.

Other features, elements, characteristics and advantages of the present invention will become more apparent from the following detailed description of preferred embodiments thereof with reference to the attached drawings.

DETAILED DESCRIPTION OF PREFERRED EMBODIMENTS

An ion-generating component, an ion-generating unit, and an ion-generating apparatus according to various preferred embodiments of the present invention will be described below with reference to the attached drawings.

Figure 1:
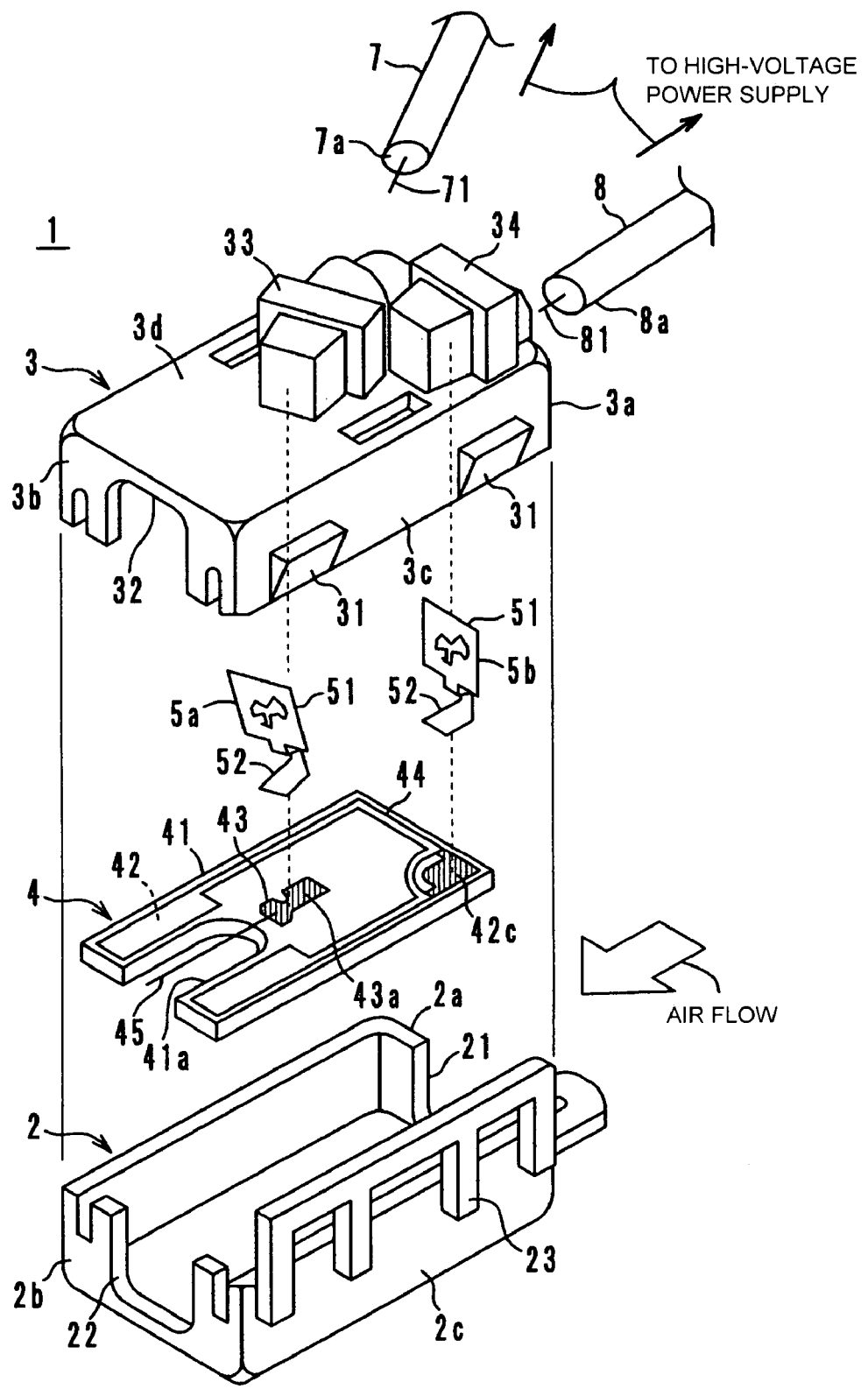
FIG. 1 is a an exploded perspective view of an ion-generating apparatus according to a preferred embodiment of the present invention.
Figure 2:
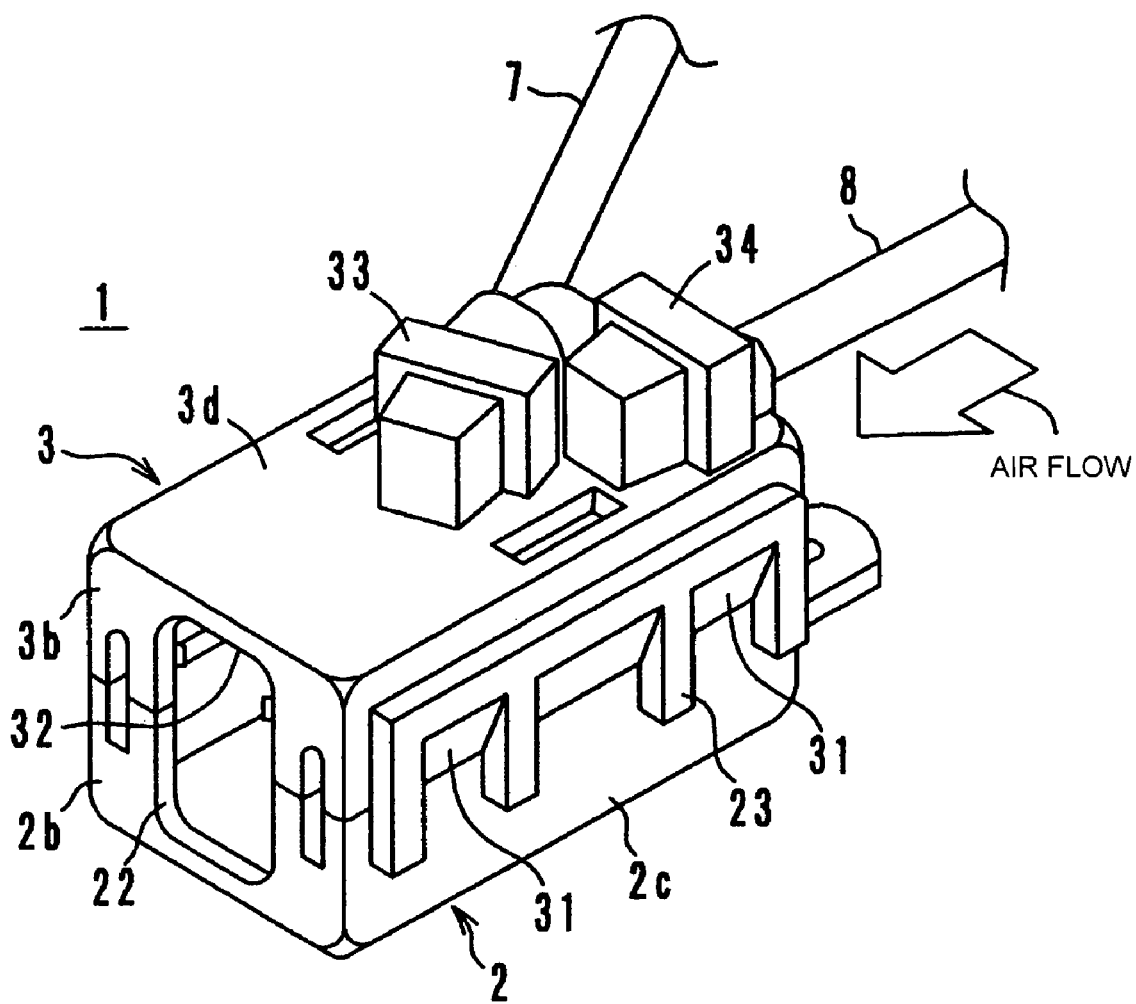
FIG. 2 is an external perspective view of the ion-generating apparatus shown in FIG. 1.

FIG. 1 is an exploded perspective view of an ion-generating apparatus 1 according to a preferred embodiment of the present invention, and FIG. 2 is an external perspective view thereof. As shown in FIG. 1, the ion-generating apparatus 1 preferably includes a lower resin case 2, an upper resin case 3, an ion-generating component 4, first and second terminals 5a and 5b made of metal, a high-voltage lead wire 7, a ground lead wire 8, and a high-voltage power supply. The lower resin case 2, the upper resin case 3, the ion-generating component 4, the first terminal 5a, and the second terminal 5b constitute an ion-generating unit.

The lower resin case 2 has an air inlet 21 provided in a side wall 2a at one end, and an air outlet 22 provided in a side wall 2b at the other end. The lower resin case 2 also has a retaining arm 23 on a front side wall 2c.

The upper resin case 3 has an air inlet (not shown) provided in a side wall 3a at one end, and an air outlet 32 provided in a side wall 3b at the other end. The upper resin case 3 also has two claws 31 on a front side wall 3c. By fitting these claws 31 in the retaining arm 23 of the lower resin case 2, the upper resin case 3 and the lower resin case 2 are firmly joined to form an air-permeable resin case. The ion-generating component 4 and the first and second terminals 5a and 5b are disposed in an accommodating space defined inside the upper resin case 3 and the lower resin case 2.

Figure 3:
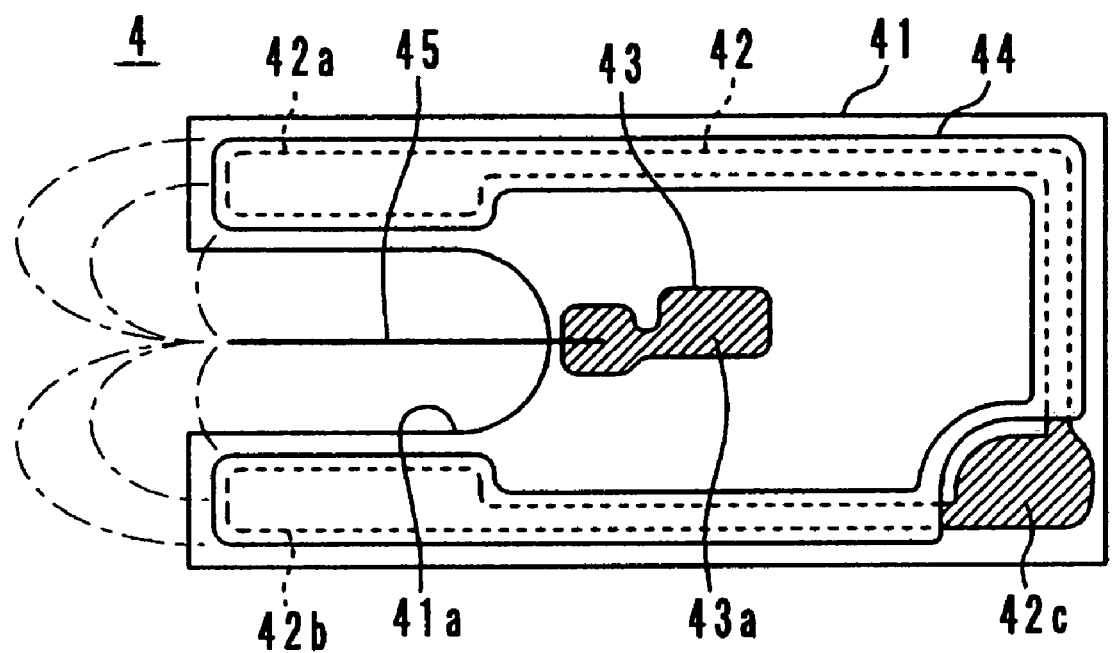
FIG. 3 is a plan view of an ion-generating component shown in FIG. 1.

As shown in FIG. 3, the ion-generating component 4 has, on a substantially rectangular insulating substrate 41, a ground electrode 42, a high-voltage electrode 43, an insulating film 44 provided on the surface of the ground electrode 42, and a wire electrode 45. A substantially U-shaped cutout 41a is formed by cutting out one side of the insulating substrate 41. The root of the wire electrode 45 is soldered to the high-voltage electrode 43, and the leading end thereof is positioned near the cutout 41a. The wire electrode 45 is preferably made of an ultrafine wire having a diameter of about 100 µm or less, for example, a piano wire, a tungsten wire, a stainless wire, or a titanium wire.

The ground electrode 42 has a pair of legs 42a and 42b arranged substantially parallel to the wire electrode 45 that are arranged with the wire electrode 45 therebetween on both sides of the cutout 41a on the insulating substrate 41. The insulating film 44 is provided on the surface of the ground electrode 42 except at a contact portion 42c which the terminal 5b touches. As the material of the insulating film 44, for example, silicone or glass glaze is preferably used. The ground electrode 42 has a resistance of approximately 50 MΩ, and is made of, for example, ruthenium oxide paste or carbon paste. Especially, ruthenium oxide is the preferred material because it does not cause migration even when an intense electric field is applied thereto.

Each of the first and second metal terminals 5a and 5b includes retaining portions 51 and foot portions 52. The retaining portions 51 are fitted in holding portions 33 and 34 provided at an upper surface 3d of the upper resin case 3. The foot portion 52 of the first terminal 5a is connected with a contact portion 43a of the high-voltage electrode 43, and the foot portion 52 of the second terminal 5b is connected with the contact portion 42c of the ground electrode 42.

An end portion 7a of the high-voltage lead wire 7 is fitted in an opening (not shown) provided in the front surface of the holding portion 33 of the upper resin case 3, and a core wire 71 is engaged with and electrically connected to the retaining portion 51 of the first terminal 5a. Similarly, an end portion 8a of the ground lead wire 8 is fitted in an opening (not shown) provided in the front surface of the holding portion 34, and a core wire 81 is engaged with and electrically connected to the retaining portion 51 of the second terminal 5b.

The high-voltage lead wire 7 is connected to a negative output terminal of the high-voltage power supply, and the ground lead wire 8 is connected to a ground output terminal of the high-voltage power supply. While the high-voltage power supply supplies a negative direct-current voltage, it may supply an alternating-current voltage obtained by superimposing negative direct-current biases. The ion-generating apparatus 1 is incorporated in, for example, an air cleaner or an air conditioner. That is, the high-voltage power supply is mounted in a power-supply controller of the air cleaner or the like, and the ion-generating unit is mounted in an air blow path, so that the air cleaner or the like blows air containing negative ions.

The ion-generating apparatus 1 having the above-described configuration can generate negative ions at a voltage of about −1.3 kV to about −2.5 kV. That is, when a negative voltage is applied to the wire electrode 45, an intense electric field is produced between the wire electrode 45 and the ground electrode 42. The air around the leading end of the wire electrode 45 is subjected to dielectric breakdown and is brought into a corona discharge state. In this case, molecules in the air are brought into a plasma state around the leading end of the wire electrode 45, and are separated into positive ions and negative ions. The positive ions in the air are absorbed by the wire electrode 45, and the negative ions remain.

When the wire electrode 45 has a thin leading end (has a small radius of curvature), electrons more easily concentrate and an intense electric field is more easily produced than when it has a thick leading end. Therefore, the use of the wire electrode 45 allows negative ions to be generated even by the application of a low voltage.

Table 1 shows the results of measurement of the number of negative ions when the voltage applied to the wire electrode 45 was changed. A known Ebert's ion counter was used for the measurement. A measurement point was set at a distance of about 30 cm on the downwind side from the ion-generating apparatus 1. The wind velocity was about 2.0 m/s. For comparison, Table 1 also shows the results of measurement of the number of negative ions generated in the known ion-generating apparatus 110 shown in FIG. 8 which has one sawtooth 112a.

TABLE 1

| Applied Voltage (kV) | Comparative Example | Preferred Embodiments (unit: ×10$^4$/cc) |
|---|---|---|
| −1.50 | 0.1 or less | 10–50 |
| −1.75 | 0.1 or less | 50–95 |
| −2.00 | 0.1 or less | 60–120 |
| −2.25 | 0.1 or less | 120 or more |
| −2.50 | 0.1 or less | 120 or more |
| −2.75 | 0.1 or less | 120 or more |
| −3.00 | 0.1 or less | 120 or more |
| −3.25 | 0.1 or less | 120 or more |
| −3.50 | 10–20 | 120 or more |
| −3.75 | 60–100 | 120 or more |

Table 1 reveals that the ion-generating apparatus 1 of the first preferred embodiment generates a sufficient number of negative ions at low voltages. While the measurement results are data obtained when the ground electrode 42 was covered with the insulating film 44, substantially equal values were obtained when the insulating film 44 was not provided.

Figure 8:
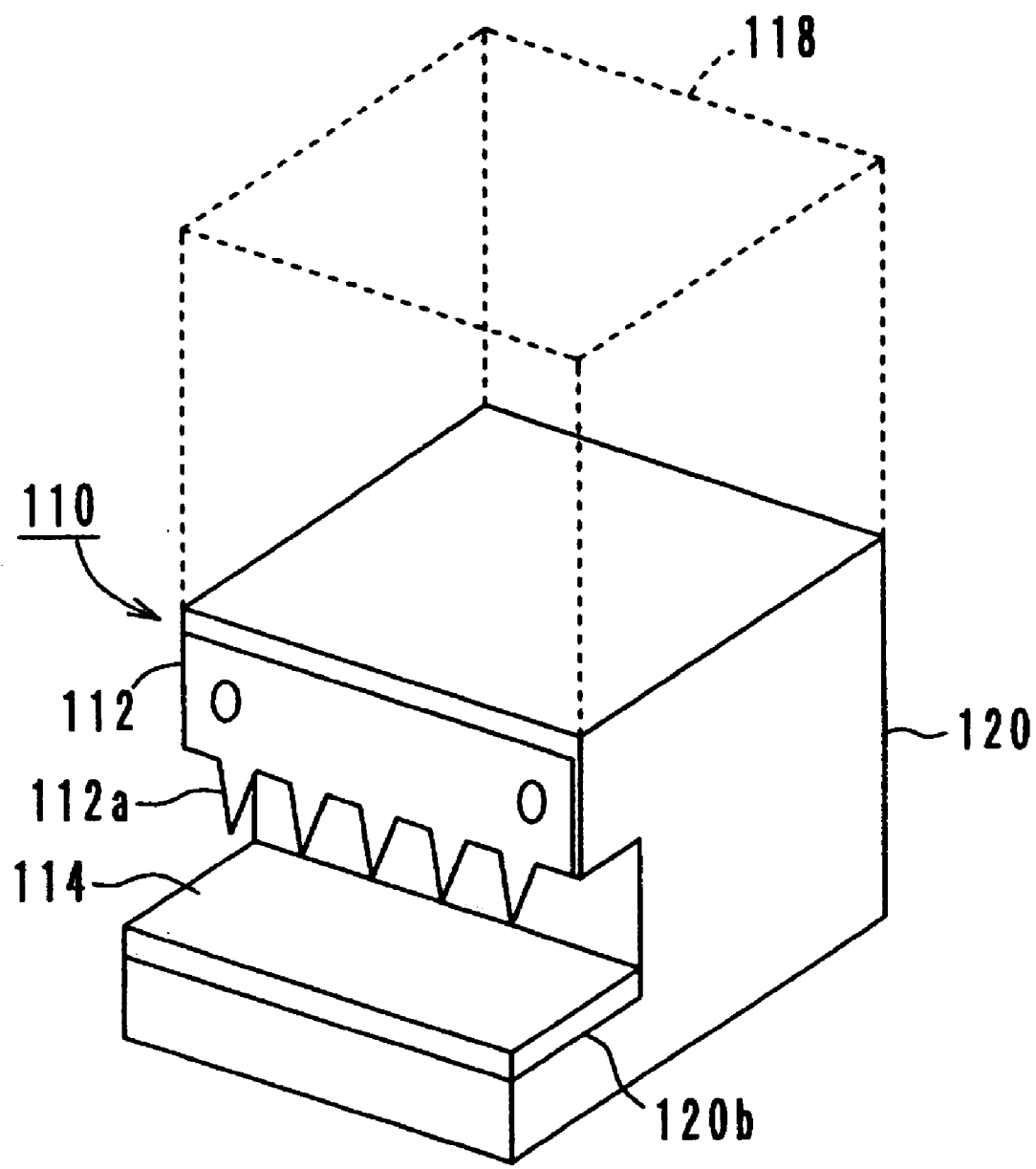
FIG. 8 is an external perspective view of a known ion-generating apparatus.

Since the sawtooth 112a of the known ion-generating apparatus 110 shown in FIG. 8 is shaped like a top-sharpened pencil, the leading end thereof changes with time, that is, becomes dull with use, and the radius of curvature gradually increases just as if the tip of the pencil was rounded. For this reason, the number of ions to be generated decreases as the radius of curvature increases.

In contrast, since the wire electrode 45 in the first preferred embodiment has a fixed diameter, the radius of curvature thereof does not change with time. Therefore, the number of ions to be generated is constant.

Figure 4:
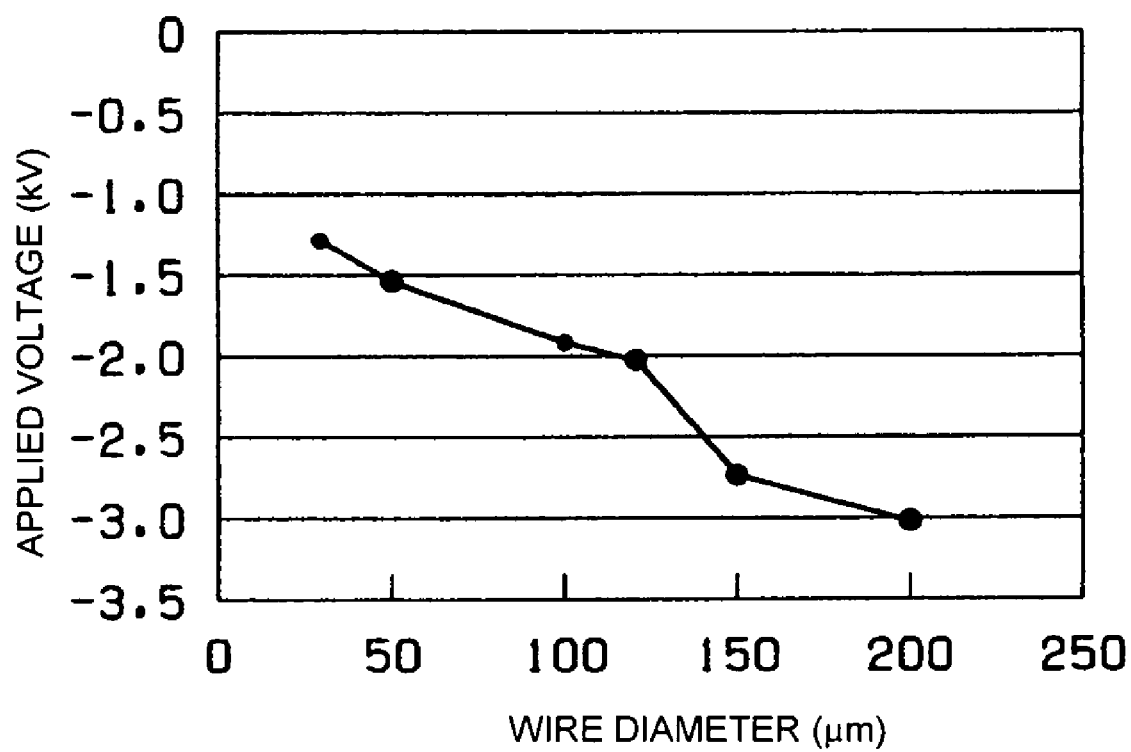
FIG. 4 is a graph showing the relationship between the applied voltage and the diameter of a wire electrode that satisfies the condition that the number of generated ions is about 1,000,000/cc.

FIG. 4 is a graph showing the relationship between the applied voltage and the diameter of the wire electrode 45 that satisfies the condition that the number of ions to be generated should preferably be approximately 1,000,000/cc. A measurement point was set at a distance of about 50 cm on the downwind side from the ion-generating apparatus 1. The wind velocity was about 3.0 m/s. As shown in the graph, a sufficient number of negative ions are generated at a low voltage of approximately −2.0 kV as long as the diameter of the wire electrode 45 is about 100 μm or less.

Figure 5A:
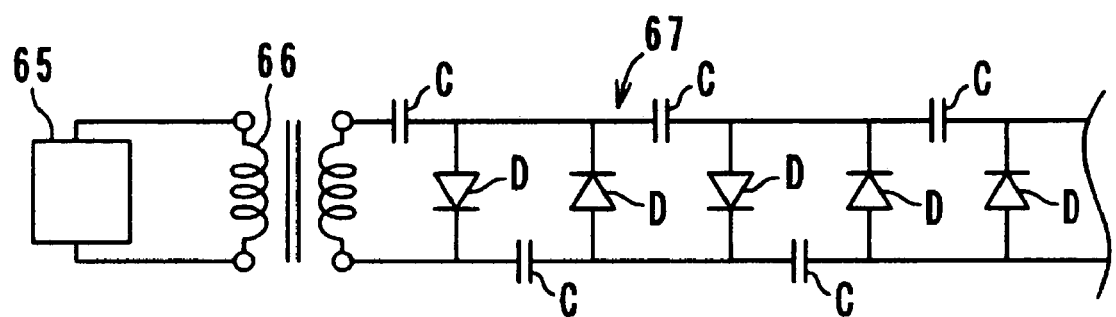
FIGS. 5A and 5B are circuit diagrams of a high-voltage power supply.
Figure 5B:
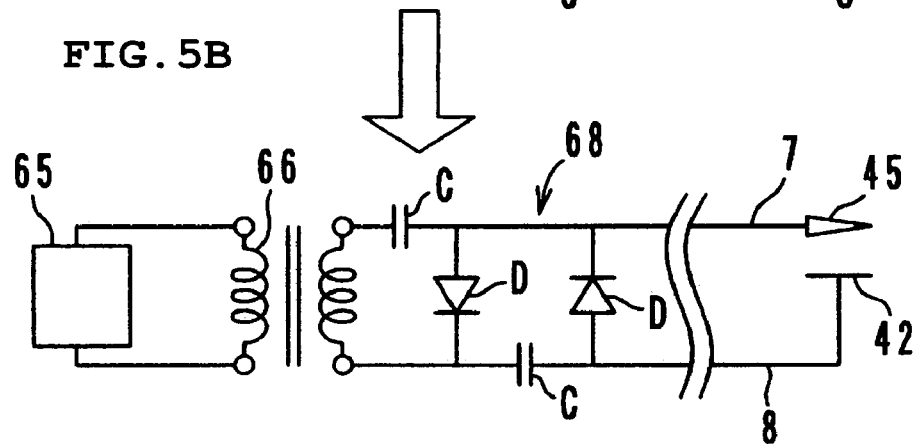

Since the voltage applied to the wire electrode 45 can be decreased, the cost of the high-voltage power supply can be increased. In general, the power supply circuit and the insulating structure can be simplified when the absolute value of the output voltage is about 2.5 kV or less. For example, a case will be considered in which an alternating voltage generated by an alternating-current circuit 65 is increased by a transformer 66, and is further increased by a Cockcroft-Walton voltage multiplier circuit (a circuit that performs rectification and boosting with a combination of capacitors C and diodes D), as shown in FIGS. 5A and 5B. In this case, in the known ion-generating apparatus, it is necessary to increase the voltage to about −1 kV to about −1.5 kV by the transformer 66 and to then multiply the voltage by five, that is increase the voltage to approximately about −5 to about −7.5 kV by a Cockcroft-Walton voltage multiplier circuit 67 shown in FIG. 5A. In contrast, in the ion-generating apparatus 1 of the first preferred embodiment, it is only necessary to double the voltage, that is, increase the voltage to approximately about −2 kV to about −3 kV by a Cockcroft-Walton voltage multiplier circuit 68 shown in FIG. 5B. Therefore, the number of the capacitors C and the diodes D in the Cockcroft-Walton voltage multiplier circuit can be reduced, and the circuit is simplified.

Moreover, since the applied voltage can be made lower than before, safety can be promoted. Since the wire electrode 45 and the ground electrode 42 are two-dimensionally arranged on the insulating substrate 41, the occupied volume is reduced, and size reduction is possible.

Table 2 shows the results of measurement of the amount of ozone generated when the voltage applied to the wire electrode 45 was changed. A measurement point was set at a distance of 5 mm from the ion-generating apparatus 1. The wind velocity was 0 m/s. For comparison, Table 2 also shows the results of measurement of the amount of ozone generated in the known ion-generating apparatus 110 shown in FIG. 8 which has one sawtooth 112a.

TABLE 2

| Applied Voltage (kV) | Comparative Example | Preferred Embodiment Insulating Film 44 Not provided | Preferred Embodiment Insulating Film 44 Provided |
|---|---|---|---|
| −2.5 | — | 0.01 or less | 0.01 or less |
| −3.0 | — | 4.0–5.0 | 0.01 or less |
| −3.5 | 0.01 or less | 5.0 or more | 0.01 or less |
| −4.0 | 0.01 or less | 5.0 or more | 0.01 or less |
| −4.5 | 0.8–1.0 | 5.0 or more | 0.01 or less |
| −5.0 | 2.2–2.5 | 5.0 or more | 0.01 or less |

(unit: ppm)

Table 2 reveals that the ion-generating apparatus 1 of the first preferred embodiment generates an extremely small amount of ozone during use. Furthermore, since the insulating film 44 is provided to cover the ground electrode 42, the discharge starting voltage between the ground electrode 42 and the wire electrode 45 can be made higher than when only air is provided therebetween. As a result, it is possible to reduce dark current (leakage current, not discharged current) flowing between the leading end of the wire electrode 45 and the ground electrode 42. Consequently, it is possible to reduce the amount of ozone generated in proportion to the amount of current.

Since the ground electrode 42 is covered with the insulating film 44, problems such as anomalous discharging, between the ground electrode 42 and the wire electrode 45 can be prevented even when the distance therebetween is reduced by the request for size reduction.

Figure 6:
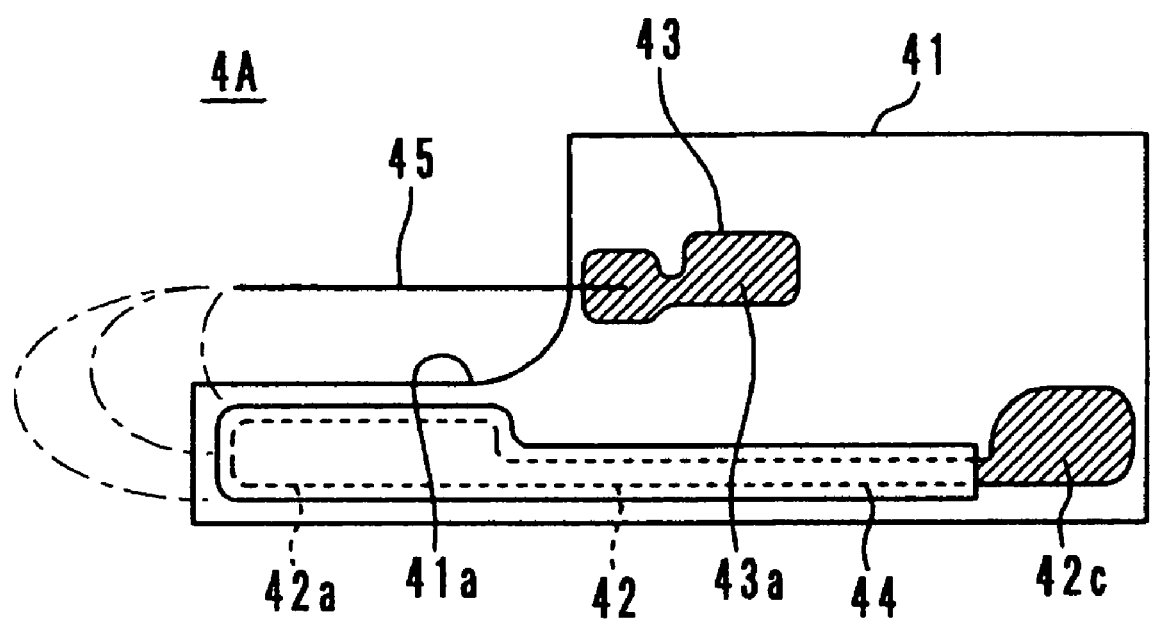
FIG. 6 is a plan view of an ion-generating component according to another preferred embodiment of the present invention.

FIG. 6 is a plan view of an ion-generating component 4A in another preferred embodiment of the present invention. A ground electrode 42 of the ion-generating component 4A has only one leg 42a that is substantially parallel to a wire electrode 45. While the number of negative ions generated by the ion-generating component 4A is slightly smaller than that in the ion-generating component 4 in the first preferred embodiment, the size can be further reduced.

Figure 7:
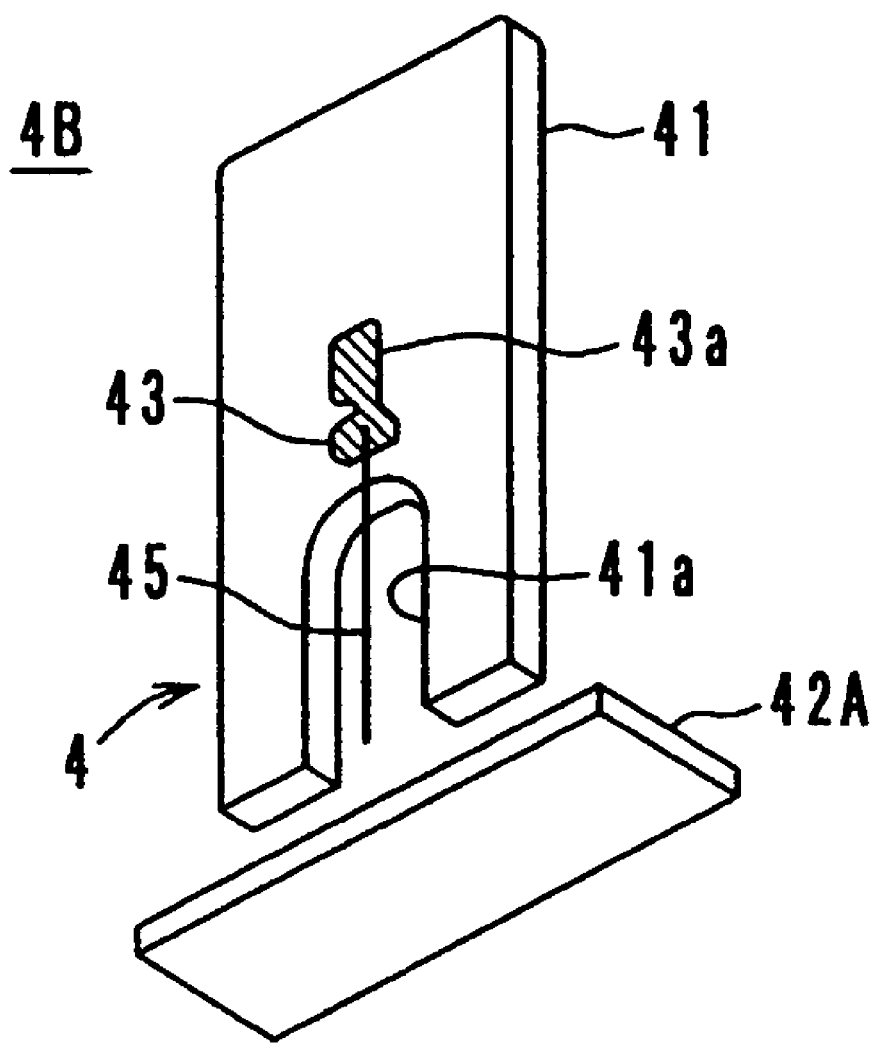
FIG. 7 is an external perspective view of an ion-generating component according to a further preferred embodiment of the present invention.

FIG. 7 is a perspective view of an ion-generating component 4B according to a further preferred embodiment of the present invention. In the ion-generating component 4B, a high-voltage electrode 43 is provided on an insulating substrate 41, and a wire electrode is soldered to the high-voltage electrode 43.

On the other hand, a ground electrode 42A is formed by coating the surface of a metal plate with an insulating film. The ground electrode 42A is disposed substantially perpendicularly to the longitudinal direction of the wire electrode 45, so that the flexibility in arranging the wire electrode 45 and the ground electrode 42A is increased.

The present invention is not limited to the above-described preferred embodiments, and various modifications are possible within the scope of the present invention. For example, while the ion-generating components of the above-described preferred embodiments have only one wire electrode, they may have two or more wire electrodes. However, when two or more wire electrodes are provided, it is necessary to pay attention to the distance therebetween because the electric field distribution is disturbed and the discharging efficiency is reduced when the distance is too short.

While the present invention has been described with reference to what are presently considered to be the preferred embodiments, it is to be understood that the invention is not limited to the disclosed preferred embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An ion-generating component comprising:
an insulating substrate;
a wire electrode having a diameter of about 100 μm or less and mounted on the insulating substrate; and
a ground electrode opposing the wire electrode; wherein
only a root end of the wire electrode is mounted on the insulating substrate, and a leading end of the wire electrode is spaced away from the insulating substrate and completely surrounded by air;
the ground electrode is provided on the insulating substrate; and
the insulating substrate has a cutout at one side, the leading end of the wire electrode is positioned near the cutout, and the ground electrode has two legs extending substantially parallel to the wire electrode and on both sides of the cutout and the wire electrode.

2. An ion-generating component according to claim 1, further comprising an insulating film provided on a surface of the ground electrode.

3. An ion-generating component according to claim 1, wherein the ground electrode is made of a resistor material.

4. An ion-generating unit comprising:
an ion-generating component according to claim 1;
a high-voltage electrode provided on the insulating substrate and connected to the wire electrode;
a first terminal in contact with the high-voltage electrode and having a retaining portion for a lead wire;
a second terminal in contact with the ground electrode and having a retaining portion for another lead wire; and
a case for accommodating the ion-generating component, the high-voltage electrode, the first terminal, and the second terminal.

5. An ion-generating apparatus comprising:
an ion-generating component according to claim 1; and
a high-voltage power supply for generating a negative voltage.

6. An ion-generating apparatus comprising:
an ion-generating unit according to claim 4; and
a high-voltage power supply that has lead wires respectively retained by the first terminal and the second terminal and that generates a negative voltage.

7. An ion-generating apparatus according to claim 5, wherein the absolute value of the voltage output from the high-voltage power supply is 2.5 kV or less.

8. An ion-generating component according to claim 1, wherein the wire electrode is made of one of a piano wire, a tungsten wire, a stainless wire, and a titanium wire.

9. An ion-generating component according to claim 1, wherein the insulating substrate includes one of silicone and glass glaze.

10. An ion-generating component according to claim 1, wherein the ground electrode has a resistance of approximately 50 MΩ.

11. An ion-generating component according to claim 1, wherein the ground electrode is made of one of ruthenium oxide paste and carbon paste.

12. An ion-generating component comprising:
an insulating substrate;
a wire electrode having a diameter of about 100 μm or less and mounted on the insulating substrate; and
a ground electrode opposing the wire electrode; wherein
only a root end of the wire electrode is mounted on the insulating substrate, and a leading end of the wire electrode is spaced away from the insulating substrate and completely surrounded by air;
the ground electrode is provided on the insulating substrate; and
the insulating substrate has a cutout at one side, the leading end of the wire electrode is positioned near the cutout, and the ground electrode has a single leg extending substantially parallel to the wire electrode.

13. An ion-generating component according to claim 1, further comprising a high-voltage electrode provided on the insulating substrate, and the wire electrode is connected to the high-voltage electrode.

* * * * *